United States Patent [19]

Knopf

[11] Patent Number: 5,396,049
[45] Date of Patent: Mar. 7, 1995

[54] STERILIZATION APPARATUS USING ELECTRICALLY HEATED INERT MATERIAL AS STERILIZING MEDIA

[75] Inventor: Ulrich C. Knopf, Meyriez, Switzerland

[73] Assignee: Agrogen, Inc., Freiburg, Switzerland

[21] Appl. No.: 987,735

[22] Filed: Dec. 8, 1992

[51] Int. Cl.⁶ .................. A61L 2/04; H05B 3/00
[52] U.S. Cl. ..................... 219/521; 219/385; 422/307; 432/215
[58] Field of Search .......... 219/521, 385, 421, 436, 219/438, 386; 422/1, 307; 432/215

[56] References Cited

U.S. PATENT DOCUMENTS

| | | | |
|---|---|---|---|
| 1,295,045 | 2/1919 | Lidberg | 219/521 X |
| 1,762,171 | 6/1930 | Goldsmith | 219/521 X |
| 1,824,585 | 9/1931 | Wolcott et al. | 219/521 |
| 2,095,154 | 10/1937 | Scott | 219/521 X |
| 2,689,904 | 9/1954 | Melton | 219/436 X |
| 2,708,710 | 5/1955 | De Verter | 219/421 X |
| 3,196,251 | 7/1965 | De Bruyne | 219/521 |
| 3,430,032 | 2/1969 | Morey | 219/436 X |
| 3,790,749 | 2/1974 | Lee | 219/521 X |
| 4,054,376 | 10/1977 | Wareham | 432/215 X |
| 4,896,023 | 1/1990 | Uchiyama | 219/521 |
| 5,068,085 | 11/1991 | Hastings | 422/1 |
| 5,073,697 | 12/1991 | Uchiyama | 219/521 X |
| 5,286,951 | 2/1994 | Jones | 219/521 |

*Primary Examiner*—Bruce A. Reynolds
*Assistant Examiner*—John A. Jeffery
*Attorney, Agent, or Firm*—Frank P. Presta

[57] ABSTRACT

A sterilization apparatus for sterilizing medical instruments such as scalpels, tweezers, needles and the like utilizes an electrically heated inert material as the sterilizing media. Instruments to be sterilized are positioned in the inert material and become aseptic within 10 to 30 seconds. The sterilization apparatus includes a cylindrical metal tube which can be electrically heated in a short time to a high temperature (200°–300° C.). The sterilization apparatus also includes insulation surrounding the heated cylindrical metal tube and an insulated base. This insulation ensures that heat is conducted to the inside of the tube and is isolated from other parts of the apparatus, particularly, the electronic components. With this insulation, a compact sterilization apparatus can be made without damage to the apparatus components due to excessive heat.

14 Claims, 3 Drawing Sheets

5,396,049

STERILIZATION APPARATUS USING ELECTRICALLY HEATED INERT MATERIAL AS STERILIZING MEDIA

BACKGROUND OF THE INVENTION

The aseptic work with instruments such as scalpels, tweezers, spatulas, scissors, tongs and needles is a prerequisite, for certain works not only in human, dental, veterinary medicine, but also in certain fields of biotechnology, in laboratories, in which plant and animal tissues are being propagated in vitro, or on which certain manipulations are being made. To these classic fields in which aseptic work is necessary on a regular and repetitive basis, others were added during recent years. This is because of the existing or possible contamination with infectious, dangerous pathogens (for example the HIV virus). To the new fields belong, for example, cosmetic works and operations, for which disinfection of the working tools are more and more requested.

The disinfection of instruments such as scalpels, tweezers, spatulas, scissors, tongs and needles (without excluding with this enumeration other tools) is essentially possible in different ways. In hospitals, medical, dental and veterinary cabinets one uses in particular the sterilization under pressure (1 atm) and heat (110°–120° C.) during 20 to 60 minutes in so-called autoclaves, or sterilization in hot air incubators with 200° C., during 3–4 hours. While these procedures are reliable for achieving asepsis, they are, from the point of view of the cost of the sterilization apparatus, the time period (20 minutes up to several hours) and the space needed, relatively expensive and therefore not accessible for everyone and not usable in every working environment. This is the reason why the sterilization of instruments with autoclaves and hot air sterilizers has been used up to date almost exclusively in well-equipped hospitals, cabinets and laboratories, with sufficient financial means and space.

Particular problems with the sterilization of instruments occur however, where, as a result of lack of space (for example in the relatively small aseptic hoods, the so-called laminar flow cabinets), or within an often repeated procedure, the same instruments have to be sterilized over and over again within a short period of time, as is the case, for example, in the work with aseptic cell and tissue cultures in the biotechnological laboratory. In this work for the sterilization of the instruments one uses mostly the flame (bunsen burner) followed by dipping the instrument in a cooling, aseptic liquid. This procedure is also reliable with regard to achieving asepsis. However, it leads on one hand to undesirable depreciation effects on the repeatedly heated instruments. On the other hand, the procedure bears a considerable risk for burn-type accidents because of the use of flame. The latter, in particular, if the aseptic liquid is inflammable, as for example the often used 70% ethanol.

The sterilization of instruments, therefore, is a problem, where, as a result of lacking financial means, expensive apparatus for sterilization cannot be bought at all, or not in a sufficient quantity, and where as a consequence the sterilization process is insufficient or omitted so that an increased risk for the transmittance of pathogens exists.

SUMMARY OF THE INVENTION

The present invention concerns an economical, small sterilization apparatus, which allows the partial or entire sterilization of instruments such as forceps, clamps, scissors, needles, tongs, razor blades, etc. in a small space and in a very short time (10–30 seconds). The instruments can be sterilized efficiently and sufficiently for many uses for which there is a danger for contamination upon contact.

The sterilization apparatus of the present invention comprises a cylindrical tube which can be heated in a short time to a high temperature (200°–300° C.) and which is protected on its outside by an optimal insulation. This insures that the heat will be preferably conducted to the inside of the tube and thus is isolated from other parts of the apparatus, for example the electronic and electricity conducting parts, and also the casing, which will not be heated to over 50° C. In this way, the parts of the apparatus which do not support a temperature over 60° C. will not be damaged and the parts around the apparatus, or the surface on which the apparatus has been installed and the users of the apparatus are not endangered by overheating (danger of a fire) or burns. The metal tube preferably is filled with an inert, high temperature supporting, heat conducting material (for example sand beads, glass beads, etc.) in which, after heating this material to about 250° C., the instruments to be sterilized will be positioned for a very short period (10–30 seconds) of time so that they will be immediately heated to a temperature of 250° C. at their contact surface.

The metal tube is surrounded by an electrical heating cuff containing resistance wires. The electrical heating cuff and metal tube are surrounded by a substantially cylindrical tube of insulating material. The cylindrical tube of insulating material is in engagement with an upper part of the casing tube so that heat generated by the heating cuff is transmitted to the metal tube and inert material inside the tube rather than other parts of the casing. A flat base plate, secured to the casing, supports the cylindrical tube. The flat base plate can include an insulating plate so that heat transmitted from the heating cuff will be transmitted principally into the metal tube and not to electronic and electricity-conducting parts or to the casing. Accordingly, the microorganisms (viruses, bacteria, microscopic fungi, etc.) will be killed within a very short period of time (seconds) which results in effective sterilization of the instruments.

BRIEF DESCRIPTION OF THE DRAWINGS

A preferred embodiment of the instrument is shown in FIGS. 1–3, without intending that the invention shall be limited in any way.

DESCRIPTION OF THE PREFERRED EMBODIMENTS

Figure 1:
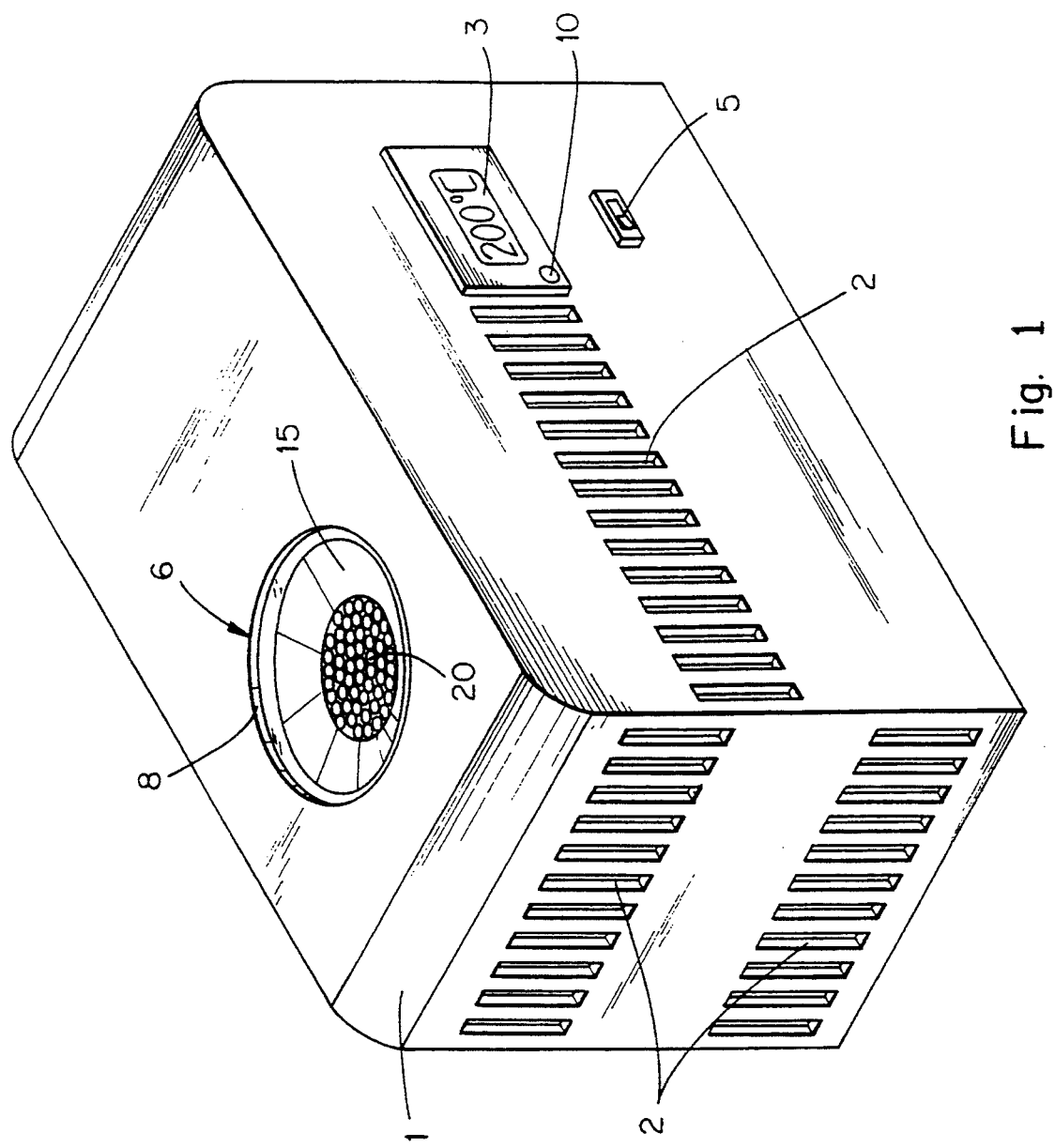
FIG. 1 is an exterior perspective view of the instrument.

FIG. 1 shows the exterior of one embodiment of the sterilization apparatus, comprising a metal casing (1), with its cooling slots (2), a temperature indicator (3), which is connected to a microprocessor (4), a switch for the electrical current (5), and an opening (6) in the casing (1), through which the user has access to the sterilization vessel (7). A metal cuff (15) is provided to hold the insulating tube (8) in a desired position. The top wall part of the casing (1) engages the insulating tube to hold it in the desired position. The temperature can be adjusted with a push button or the like on the microprocessor.

Figure 2:
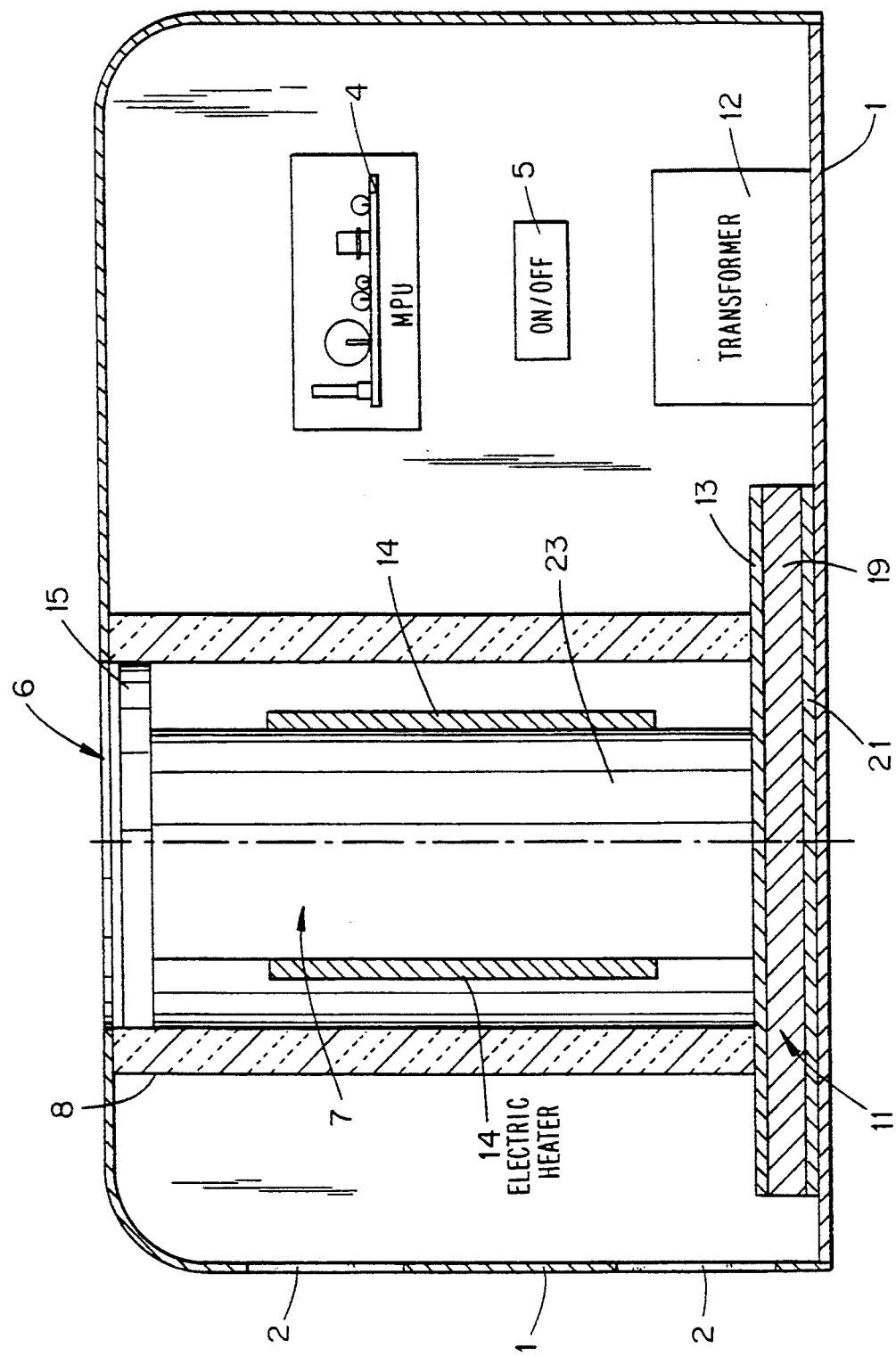
FIG. 2 is an elevational view in cross-section of the apparatus.

FIG. 2 illustrates the insulating tube (8) which is engaged and pushed downwardly by the top wall of the casing (1) and in this way held in position, the sterilization vessel (7), a flat, insulating base plate (11) comprising parts (13), (19) and (21) (see FIG. 3), a transformer (12) or the like needed for the operation of the microprocessor (4), which after setting of the temperature starts the current for the heating cuff (14), or stops it and thus regulates the inside temperature of the sterilization vessel.

Figure 3:
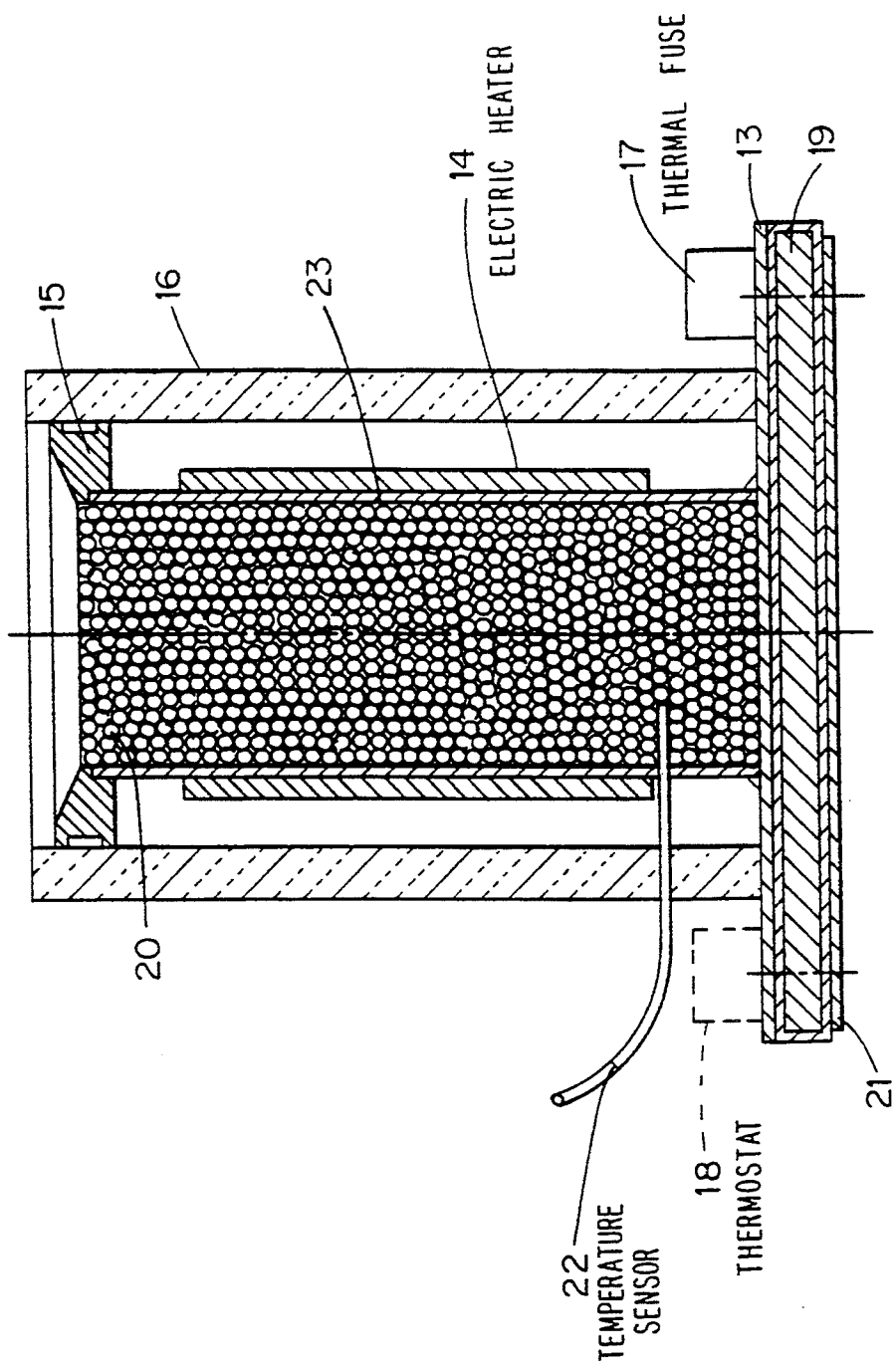
FIG. 3 is an elevational view in cross-section of the sterilization vessel after removing it from the case of the apparatus.

FIG. 3 shows the sterilization vessel (7) taken out of the casing (1). It comprises a metal tube (23) which at its lower end has been firmly fixed on to a metal plate (13). Before heating, the metal tube is filled with an inert material, for example, glass beads (20). The metal tube (23) is surrounded by a heating cuff (14). At the upper end, a metal cuff (15) is secured to the metal tube to insure that the inert material (for example glass beads) will not enter the compartment of the heating cuff (14), and also to position the insulating tube (16) a desired distance from the metal tube (23). The cuff (15) also acts as a heat-barrier on the top.

A temperature probe (22) connected to the microprocessor (4) penetrates in to the metal tube (23) and the inert material (20) to measure the temperature thereof. A safety fuse (17) is mounted on the metal plate (13) to prevent continued heating of the apparatus after failure of the electronic temperature regulation device. On the metal plate (13) an additional bimetallic thermostat (18) could be installed, if the more expensive electronic temperature regulation device will be replaced by an inexpensive bimetallic thermostat regulator. The metal plate (13) is protected at the bottom by an insulating plate (19) which is supported towards the bottom with a metal sheet (21). The metal plate (13), the metal tube (23), the insulating plate (19) and the metal sheet (21) are all firmly connected to each other, the metal sheet (21) attached to the base (27) of the casing (see FIG. 2).

In the use of the apparatus of the present invention, it is first connected to electrical current at the work place. The microprocessor (4) is then set so that the glass beads (20) in the metal tube (23) are heated to a suitable high temperature (250° C.). This happens within a few minutes. Thereafter, the instruments to be sterilized (not shown) are positioned for a very short time (10–30 seconds) in the hot glass beads, whereby they will be sterilized at the contact-surface within a very short period of time. Thereafter the instruments so sterilized can be used immediately, or they can be dipped without any danger into an aseptic cooling solution, if desired, before use. After use, one and the same instrument, for example a tweezer needed for the transplantation of in vitro cultivated tissues, can be sterilized many times a day directly at the working place (in the laminar flow cabinet), within a very short period of time and repeatedly used.

The difficulty in the construction of such an apparatus remains in the condition that the apparatus must heat the metal tube to relatively high temperatures (220°–300° C.) and that the tube must be placed in a small casing, in spaced relation to other necessary parts of the apparatus, in particular the electronic components and the electrical wires, or the casing, which can be damaged by excessive heat and/or become a hazard (burns, fire) for the user. The solution of the problem makes it necessary that the material has to be chosen and manufactured so that at maximum metal tube temperature (280° C.) the casing and the inside of the casing are not heated to over 50° C. On one hand, this problem is solved through the construction of the sterilization vessel, in particular also the metal cuff (15), the choice of the insulating material (aluminum silicate with or without iron oxide or titanium oxide), the construction and the shape of the insulating tube (16) and finally the construction of the casing (1). The insulating material preferably is shaped with heat, pressure and a binding material, into the cylindrical tube (16) before its assembly. The insulating tube (16) surrounds the metal tube and the heating cuff and, by engagement with the top wall of the casing (1), is urged downwardly into engagement with the insulating plate (11). Through the pressure exerted by the casing cover on the insulating tube, a gap between the sterilization vessel (7) and the casing is avoided, thereby insuring that no inert material (for example glass beads) can penetrate into the inside of the casing. This must be avoided, because the inert material has to be cleaned, or changed from time to time.

On the other hand, part of the heat of the insulating tube will be transferred on to the casing and thus will be irradiated towards the outside and not the inside. The heat rejecting, stiff, insulating material (aluminum silicate with or without iron or titanium oxide) is being used also in a flat form for insulating the metal tube (23) fixed onto the metal plate (13) towards the bottom of the metal casing. The insulating material (19) is pressed between the metal plate (13) and the metal sheet (21). The insulating material (19) and insulating tube (16) can be made out of a pressed, formed stiff material made of silicon oxide, iron oxide, titanium oxide and aluminum oxide enclosed by a foil (30) (see FIG. 3). Thereafter the entire construction can directly be screwed or otherwise attached to the bottom (27) of the casing (lower part of the casing). In this way, it is possible to construct a small and at the same time optimally insulated apparatus.

The metal plate (13) serves as a base plate (bottom) for the metal tube (23), as well as a support for the installation of an replaceable safety fuse (17) and bimetallic thermostat (18). In this way, the metal plate linked to the heated metal tube functions not only as mechanical fixing element, but at the same time as a heat conducting medium. This construction allows the dimensions of the apparatus to be maintained at a minimum and also provides for a reduced manufacturing cost. In addition, it makes it possible to easily replace if necessary the bimetallic thermostats or fuses which have only a limited life time.

The use of a microprocessor (4) together with a metal tube temperature probe (22) allows for a rapid exact, continuous, electrical current-saving regulation of the temperature of the inert material (20) in the heated metal tube (23).

The replacement of the electronic temperature regulation using the microprocessor (4), by means of the small bimetallic thermostat (18) could occur where a rapid, precise regulation and control of the temperature is not necessary. This version is certainly less expensive, because the microprocessor (4) and the necessary transformer (12), the electronic temperature indicator (3) and the temperature probe (22) can be omitted; but this modified apparatus will not equal the electronic embodiment in terms of safety, function (asepsis of the instruments) and the lifetime of the apparatus (bimetallic thermostats do have a limited life span).

I claim:

1. Apparatus for sterilizing and incubating instruments for biological and medical use, comprising a casing, and an electrically heated and temperature regulated metal vessel in said casing comprising:
   a) a metal tube surrounded by an electrical heating cuff, said metal tube filled with an inert heat conducting material;
   b) an insulating tube surrounding said metal tube and spaced therefrom to form a gap between said metal tube and electrical heating cuff and said insulating tube, said insulating tube engaging a top wall of said casing;
   c) a insulating base supporting said metal tube and said insulating tube,
   d) wherein said casing includes an opening for access to said inert heat conducting material, said insulating base, and said insulating tube housed by said casing.

2. Apparatus according to claim 1, wherein said metal tube is made of a heat conducting metal, and said insulating base comprises an insulating layer disposed between two metal plates.

3. Apparatus according to claim 1, wherein said insulating base rests on a bottom of said casing.

4. Apparatus according to claim 1, further comprising a circular metal cuff surrounding one end of said metal tube.

5. Apparatus according to claim 4, wherein the metal cuff separates said insulating tube from said metal tube to form said gap.

6. Apparatus according to claim 5, wherein the heated metal tube and the inert material, the metal cuff and the insulating tube are so constructed and positioned that other parts of the apparatus and the casing do not exceed 50° C. even when the metal tube is heated to a temperature of over 200° C.

7. Apparatus according to claim 1, wherein the insulating plate has mounted on a portion thereof and spaced from the metal tube a thermostat means for limiting the maximum temperature of the apparatus by interruption of electrical heating current.

8. Apparatus according to claim 1, wherein said insulating tube and said insulating plate comprise stiff fibers of aluminum silicate solidified by a binding agent.

9. Apparatus according to claim 1, wherein said insulating tube and said insulating plate are made out of a pressed, formed, stiff material made of silicon oxide, iron oxide, titanium oxide and aluminum oxide enclosed by a foil.

10. Apparatus according to claim 1, wherein said inert heat conducting material comprises glass beads of a diameter up to 3 mm.

11. Apparatus according to claim 1, wherein the inert heat conducting material comprises sand grains.

12. Apparatus according to claim 1, wherein the inert heat conducting material comprises graphite grains.

13. Apparatus according to claim 1, further comprising means for electrical heating of the metal tube comprising a temperature probe which measures the temperature of the inert heat conducting material inside the metal tube, and a microprocessor means for controlling the temperature of the inert heat conducting material, so that it is maintained at a preset value.

14. Apparatus according to claim 13, wherein said microprocessor means further comprises means for setting a working temperature and wherein said casing has a means for indicating a temperature inside said metal vessel which can be read from the outside of said casing.

* * * * *